(12) United States Patent
Sanganee et al.

(10) Patent No.: US 7,238,691 B2
(45) Date of Patent: Jul. 3, 2007

(54) PIPERIDINE DERIVATIVES AND THEIR USE AS MODULATORS OF CHEMOKINE (ESPECIALLY CCR3) ACTIVITY

(75) Inventors: Hitesh Sanganee, Loughborough (GB); Brian Springthorpe, Loughborough (GB)

(73) Assignee: AstraZeneca AB, Södertälje (SE)

( * ) Notice: Subject to any disclaimer, the term of this patent is extended or adjusted under 35 U.S.C. 154(b) by 591 days.

(21) Appl. No.: 10/489,811

(22) PCT Filed: Sep. 12, 2002

(86) PCT No.: PCT/SE02/01651

§ 371 (c)(1),
(2), (4) Date: Mar. 17, 2004

(87) PCT Pub. No.: WO03/024962

PCT Pub. Date: Mar. 27, 2003

(65) Prior Publication Data

US 2004/0242577 A1 Dec. 2, 2004

(30) Foreign Application Priority Data

Sep. 18, 2001 (GB) .................. 0122503.6

(51) Int. Cl.
*A61K 31/5377* (2006.01)
*C07D 413/06* (2006.01)
(52) U.S. Cl. .................. 514/231.5; 544/129
(58) Field of Classification Search ............... 544/129; 514/231.5
See application file for complete search history.

(56) References Cited

U.S. PATENT DOCUMENTS

| | | | |
|---|---|---|---|
| 4,695,575 A | 9/1987 | Janssens et al. | |
| 5,883,096 A | 3/1999 | Lowe et al. | |
| 5,889,006 A | 3/1999 | Lowe et al. | |
| 5,952,349 A | 9/1999 | Asberom et al. | |
| 5,977,138 A | 11/1999 | Wang et al. | |
| 6,066,636 A | 5/2000 | Kozlowski et al. | |
| 6,387,930 B1 | 5/2002 | Baroudy et al. | |
| 6,440,440 B1 | 8/2002 | Meerpoel et al. | |
| 6,759,411 B2 * | 7/2004 | Ko et al. .................. | 514/235.5 |
| 6,903,115 B2 | 6/2005 | Rigby et al. | |

FOREIGN PATENT DOCUMENTS

| | | |
|---|---|---|
| EP | 0 099 139 | 1/1984 |
| EP | 0 121 972 | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| GB | 1250719 | 10/1971 |
| WO | WO 93/10091 | 5/1993 |
| WO | WO 95/08535 | 3/1995 |
| WO | WO 96/26196 | 8/1996 |
| WO | WO 96/34857 | 11/1996 |
| WO | WO 96/41631 | 12/1996 |
| WO | WO 97/24324 | 7/1997 |
| WO | WO 98/01425 | 1/1998 |
| WO | WO 98/05291 | 2/1998 |
| WO | WO 98/05292 | 2/1998 |
| WO | WO 98/06697 | 2/1998 |
| WO | WO 98/11128 | 3/1998 |
| WO | WO 99/04794 | 2/1999 |
| WO | WO-99/38514 | * 5/1999 |
| WO | WO 99/37304 | 7/1999 |
| WO | WO 99/38514 | 8/1999 |
| WO | WO 99/51578 | 10/1999 |
| WO | WO 00/00488 | 1/2000 |
| WO | WO 00/12478 | 3/2000 |
| WO | WO 00/32590 | 6/2000 |
| WO | WO 00/35877 | 6/2000 |
| WO | WO 00/66559 | 11/2000 |
| WO | WO 01/02381 | 1/2001 |
| WO | WO 01/07436 | 2/2001 |
| WO | WO 01/29066 | 4/2001 |
| WO | WO 01/77101 | 10/2001 |
| WO | WO 01/92227 | 12/2001 |
| WO | WO 02/18335 | 3/2002 |
| WO | WO 02/20484 | 3/2002 |
| WO | WO 02/079190 | 10/2002 |

(Continued)

OTHER PUBLICATIONS

Allain et al., (2005) STN International, HCAPLUS Database, Columbus, OH, Accession No. 1992:187881, Reg. No. 46817-91-8, citing "Antidepressants and cognition: comparative effects of moclobemide, viloxazine and maprotiline", *Psychopharmacology* 106 (Suppl.).

(Continued)

*Primary Examiner*—Kamal A. Saeed
*Assistant Examiner*—Janet L. Coppins
(74) *Attorney, Agent, or Firm*—Fish & Richardson, P.C.

(57) ABSTRACT

The invention provides a compound of formula (I): T is C(O) or S(O)$_2$; W is CH$_2$, (CH$_2$)$_2$, CH(CH$_3$), CH(CH$_3$)O or cyclopropyl; X is O, CH$_2$, C(O), S, S(O), S(O)$_2$ or NR$^3$; m is 0 or 1; R$^1$ is optionally substituted aryl or optionally substituted heterocyclyl; R$^2$ is alkyl (optionally substituted by OH), cycloalkyl, optionally substituted aryl or optionally substituted heterocyclyl; that are modulators of chemokine (especially CCR3) activity and are especially useful for treating asthma and/or rhinitis.

10 Claims, No Drawings

FOREIGN PATENT DOCUMENTS

| WO | WO 02/081449 | 10/2002 |
|----|--------------|---------|
| WO | WO 03/004487 | 1/2003 |
| WO | WO 03/018576 | 3/2003 |
| WO | WO 03/078395 | 9/2003 |
| WO | WO 03/078421 | 9/2003 |
| WO | WO 2004/029041 | 4/2004 |
| WO | WO 2004/085423 | 10/2004 |
| WO | WO 2004/087659 | 10/2004 |
| WO | WO 2004/099144 | 11/2004 |

OTHER PUBLICATIONS

Cohen et al., *Am. J. Clin. Pathol.* 105:589 (1996).

Hermans et al., "4-Substituted Piperidines. II. Reaction of 1-Benzyl-4-cyano-4-*t*-aminopiperidines with Organometallic Compounds", *J. Med. Chem.* 8(6):851-855 (1965) at p. 852 ("compound 12" in Table I).

Patani and LaVoie, "Bioisosterism: A Rational Approach in Drug Design", *Chem. Rev.* 96:3147-3176 (1996).

STN International, File CAPLUS, CAPLUS accession No. 1988:630911, Document No. 109:230911, Lehmann, Jochen et al: "Lactones. XVIII. Synthesis of lactone-bridged 1,1-diarylpropanamines"; & *Arch. Pharm.* (Weinheim, Ger.) (1988), 321(7), 443-445.

\* cited by examiner

PIPERIDINE DERIVATIVES AND THEIR USE AS MODULATORS OF CHEMOKINE (ESPECIALLY CCR3) ACTIVITY

This application claims priority under 35 U.S.C. §371 to a national phase filing of international application number PCT/SE02/01651, filed Sep. 12, 2002, which claims priority to GB 0122503.6, filed Sep. 18, 2001. These applications are incorporated by reference herein.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794 and WO00/35877.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Histamine is a basic amine, 2-(4-imidazolyl)ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, especially rhinitis and urticaria Antagonists of H1 are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

The present invention provides a compound of formula (I):

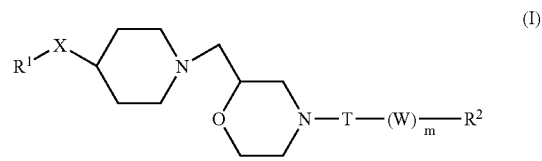

wherein:
T is C(O) or S(O)$_2$;
W is CH$_2$, (CH$_2$)$_2$, CH(CH$_3$), CH(CH$_3$)O or cyclopropyl;
X is O, CH$_2$, C(O), S, S(O), S(O)$_2$ or NR$^3$;
m is 0 or 1;
R$^1$ is optionally substituted aryl or optionally substituted heterocyclyl;
R$^2$ is alkyl (optionally substituted by OH), cycloalkyl, optionally substituted aryl or optionally substituted heterocyclyl;
wherein the foregoing aryl and heterocyclyl moieties are optionally substituted by: halogen, cyano, nitro, hydroxy, oxo, S(O)$_p$R$^4$, OC(O)NR$^5$R$^6$, NR$^7$R$^8$, NR$^9$C(O)R$^{10}$, NR$^{11}$C(O)NR$^{12}$R$^{13}$, S(O)$_2$NR$^{14}$ R$^{15}$, NR$^{16}$S(O)$_2$R$^{17}$, C(O)NR$^{18}$R$^{19}$, C(O)R$^{20}$, CO$_2$R$^{21}$, NR$^{22}$CO$_2$R$^{23}$, C$_{1-6}$ alkyl, C$_{1-6}$ haloalkyl, C$_{1-6}$ alkoxy(C$_{1-6}$)alkyl, C$_{1-6}$ alkoxy, C$_{1-6}$ haloalkoxy, C$_{1-6}$ alkoxy(C$_{1-6}$)alkoxy, C$_{1-6}$ alkylthio, C$_{2-6}$ alkenyl, C$_{2-6}$ alkynyl, C$_{3-10}$ cycloalkyl (itself optionally substituted by C$_{1-4}$ alkyl or oxo), methylenedioxy, difluoromethylenedioxy, phenyl, phenyl(C$_{1-4}$)alkyl, phenoxy, phenylthio, phenyl(C$_{1-4}$)alkoxy, heteroaryl, heteroaryl(C$_{1-4}$)alkyl, heteroaryloxy or heteroaryl(C$_{1-4}$)alkoxy; wherein any of the immediately foregoing phenyl and heteroaryl moieties are optionally substituted with halogen, hydroxy, nitro, S(O)$_q$(C$_{1-4}$ alkyl), S(O)$_2$NH$_2$, cyano, C$_{1-4}$ alkyl, C$_{1-4}$ alkoxy, C(O)NH$_2$, C(O)NH(C$_{1-4}$ alkyl), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$;
p and q are, independently, 0, 1 or 2;
R$^3$, R$^5$, R$^6$, R$^7$, R$^8$, R$^9$, R$^{10}$, R$^{11}$, R$^{12}$, R$^{13}$, R$^{14}$, Re$^{15}$, R$^{16}$, R$^{18}$, R$^{19}$ R$^{20}$, R$^{21}$ and R$^{22}$ are, independently, hydrogen, C$_{1-6}$ alkyl (optionally substituted by halogen, hydroxy or C$_{3-10}$ cycloalkyl), CH$_2$(C$_{2-6}$ alkenyl), phenyl (itself optionally substituted by halogen, hydroxy, nitro, NH$_2$, NH(C$_{1-4}$ alkyl), N(C$_{1-4}$alkyl)$_2$, S(O)$_2$(C$_{1-4}$ alkyl), S(O)$_2$NH$_2$, cyano, C$_{1-4}$ alkyl, C$_{1-4}$ alkoxy, C(O)NH$_2$, C(O)NH(C$_{1-4}$ alkyl), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^5R^6$, $NR^7R^8$, $NR^{12}R^{13}$, $NR^{14}R^{15}$, $NR^{18}R^{19}$ or groups $N(C_{1-4}$alkl)$_2$ may, independently, form a 4-7 membered heterocyclic ring, azetidine, pyrrolidine, piperidine, azepine, 1,4-morpholine or 1,4-piperazine, the latter optionally substituted by $C_{1-4}$alkyl on the distal nitrogen;

$R^4$, $R^{17}$ and $R^{23}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

or an N-oxide thereof; or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, sulfate, acetate, diacetate, fumarate, maleate, tartrate, citrate, oxalate, methanesulfonate or p-toluenesulfonate.

The compounds of the invention may exist as solvates (such as hydrates) and the present invention covers all such solvates.

Halogen includes fluorine, chlorine, bromine and iodine.

Alkyl groups and moieties are straight or branched chain and are, for example, methyl, ethyl, n-propyl, iso-propyl or tert-butyl. Alkyl preferably comprises 1-6 carbon atoms.

Alkenyl is, for example, vinyl or allyl. Alkenyl preferably comprises 2-6 carbon atoms.

Alkynyl is, for example, propargyl. Alkynyl preferably comprises 2-6 carbon atoms.

Cycloalkyl is mono-, bi or tricyclic and is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl, indanyl or tetrahydronaphthalenyl ring system).

Aryl is preferably phenyl or naphthyl.

Heterocyclyl is an aromatic or non-aromatic 5 or 6 membered ring, optionally fused to one or more other rings, comprising at least one heteroatom selected from the group comprising nitrogen, oxygen and sulfur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in 1,1-dioxo-2,3-dihydrobenz[b]thienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, dihydro-1-benzopryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4-b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8]naphthyridinyl or in 1H-[1,8]naphthyridin-4-one-yl), a benzothiazinyl (for example in 4H-benzo[1,4]thiazin-3-one-yl), benzo[d]imidazo[2,1-b]thiazol-2-yl or dibenzothiophenyl (also known as dibenzothienyl); or an N-oxide thereof (such as a pyridine N-oxide), or an S-oxide or S-dioxide thereof. Additionally heterocyclyl can be 1,2,4-oxadiazolyl, 1,2,3-triazolyl, tetrazolyl; pyridazinyl, thieno[2,3-b]pyridinyl, pyrazolo[5,1-c][1,2,4]triazinyl, purinyl, pyrazolo[1,5-a]pyrimidinyl, thieno[2;3-c]pyrazolyl or phthalazinyl.

An N-oxide of a compound of formula (I) is, for example, a 2-(1-oxy-piperidin-1-yl)methyl-morpholinyl compound.

In one particular aspect the present invention provides a compound of formula (I) wherein: T is C(O) or $S(O)_2$; W is $CH_2$, $(CH_2)_2$, $CH(CH_3)$, $CH(CH_3)0$ or cyclopropyl; X is O, $CH_2$, C(O), S, S(O), $S(O)_2$ or $NR^3$; m is 0 or 1; $R^1$ is optionally substituted aryl or optionally substituted heterocyclyl; $R^2$ is alkyl (optionally substituted by OH), cycloalkyl, optionally substituted aryl or optionally substituted heterocyclyl; wherein the foregoing aryl and heterocyclyl moieties are optionally substituted by: halogen, cyano, nitro, hydroxy, oxo, $S(d)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$) alkoxy, heteroaryl, heteroaryl($C_{1-4}$)alkyl, heteroaryloxy or heteroaryl($C_{1-4}$)alkoxy; wherein any of the immediately foregoing phenyl and heteroaryl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; p and q are, independently, 0, 1 or 2; $R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$ $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, NH$_2$, NH(C$_{1-4}$ alkyl), N(C$_{1-4}$ alkyl)$_2$, S(O)$_2$(C$_{1-4}$ alkyl), S(O)$_2$NH$_2$, cyano, C$_{1-4}$ alkyl, C$_{1-4}$ alkoxy, C(O)NH$_2$, C(O)NH(C$_{1-4}$ alkyl), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, NH$_2$, NH(C$_{1-4}$ alkyl), N(C$_{1-4}$ alkyl)$_2$, S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$, cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$, CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$); alternatively NR$^5$R$^6$, NR$^7$R$^8$, NR$^{12}$R$^{13}$, NR$^{14}$R$^{15}$, NR$^{18}$R$^{19}$, may, independently, form a 4-7 membered heterocyclic ring, azetidine, pyrrolidine, piperidine, azepine, 1,4-morpholine or 1,4-piperazine, the latter optionally substituted by C$_{1-4}$alkyl on the distal nitrogen; R$^4$, R$_{17}$ and R$^{23}$ are, independently, C$_{1-6}$ alkyl (optionally substituted by halogen, hydroxy or C$_{3-10}$ cycloalkyl), CH$_2$(C$_{2-4}$ alkenyl), phenyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ above), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ above), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ above), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ above), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ above), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ above), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$); or an N-oxide thereof; or a pharmaceutically acceptable salt thereof; or a solvate thereof.

In a further aspect X is O.

In another aspect R$^1$ is phenyl substituted with one or more of fluorine, chlorine, C$_{1-4}$ alkyl (especially methyl) or C$_{1-4}$ alkoxy (especially methoxy).

In a further aspect R$^1$ is phenyl optionally substituted (for example with one, two or three of) by halogen (especially fluoro or chloro), C$_{1-4}$ alkyl (especially methyl) or C$_{1-4}$ alkoxy (especially methoxy). In a still further aspect R$^1$ is phenyl substituted by one, two or three of: fluoro, chloro, methyl or methoxy. In a still further aspect R$^1$ is 3,4-dichlorophenyl.

In a still further aspect T is is C(O).

In another aspect m is 1 and W is CH$_2$.

In yet another aspect m is 0.

In a still further aspect R$^2$ is unsubstituted phenyl, monosubstituted phenyl, unsubstituted heterocyclyl or monosubstituted heterocyclyl, the substituents being chosen from those described above.

In another aspect R$^2$ is phenyl substituted with halogen, alkyl or alkoxy.

In yet another aspect R$^2$ is phenyl or heterocyclyl, either of which is optionally substituted by: halo, hydroxy, nitro, cyano, oxo, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{24}$ (wherein k is 0, 1 or 2 (preferably 2); and R$^{24}$ is C$_{1-4}$ alkyl, C$_{1-4}$ hydroxyalkyl, C$_{3-7}$ cycloalkyl(C$_{1-4}$ alkyl) (such as cyclopropylmethyl) or phenyl), C$_{1-4}$ haloalkylthio, C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$.

In one aspect the variable R$^2$ is phenyl optionally substituted by: halo, hydroxy, nitro, cyano, amino, C$_{1-4}$ alkyl (itself optionally substituted by S(O)$_2$(C$_{1-4}$ alkyl), S(O)$_2$phenyl), C$_{1-4}$ alkoxy, S(O)$_k$R$^{24}$ (wherein k is 0, 1 or 2 (preferably 2); and R$^{24}$ is C$_{1-4}$ alkyl, C$_{1-4}$ hydroxyalkyl, C$_{3-7}$ cycloalkyl(C$_{1-4}$ alkyl) (such as cyclopropylmethyl) or phenyl), C$_{1-4}$ haloalkylthio, C(O)NH$_2$, NHS(O)$_2$(C$_{1-4}$ alkyl), S(O)$_2$NH$_2$, S(O)$_2$NH(C$_{1-4}$ alkyl) or S(O)$_2$N(C$_{1-4}$ alkyl)$_2$ (and these alkyl groups may join to form a ring as described for R$^5$ and R$^6$ above).

In another aspect the variable R$^2$ is phenyl optionally substituted by: halo, hydroxy, nitro, cyano, amino, C$_{1-4}$ alkyl (itself optionally substituted by S(O)$_2$phenyl), C$_{1-4}$ alkoxy, S(O)$_k$R$^{24}$ (wherein k is 0, 1 or 2; and R$^{24}$ is C$_{1-4}$ alkyl or phenyl) or C$_{1-4}$ haloalkylthio.

In a further aspect R$^2$ is optionally substituted heterocyclyl; wherein heterocyclyl is thienyl, thiazolyl, pyrazolyl, isoxazolyl, 1,2,4-oxadiazolyl, 1,2,3-triazolyl, tetrazolyl, imidazolyl, pyridinyl, pyridazinyl, pyrimidinyl, benz[b]thienyl, indazolyl, benzimidazolyl, benztriazolyl, benzoxazolyl, imidazo[1,2a]pyridinyl, [1,8]naphthyridinyl, isoquinolinyl, thieno[2,3-b]pyridinyl, pyrazolo[5,1-c][1,2,4]triazinyl, purinyl, pyrazolo[1,5-a]pyrimidinyl, thieno[2,3-c]pyrazolyl or phthalazinyl; and heterocyclyl is optionally substituted by halogen (such as fluoro), C$_{1-4}$ alkyl, C$_{1-4}$ alkylthio, phenyl, thienyl, pyridinyl, CF$_3$, NH$_2$, CO$_2$(C$_{1-4}$ alkyl) or oxo.

A compound of formula (I) can be prepared by reacting a compound of formula (II):

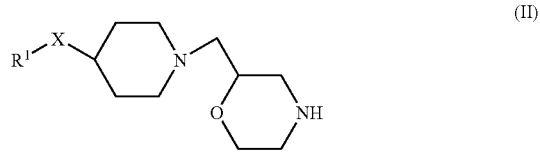

(II)

with a compound of formula L-T-(W)$_m$—R$^2$, wherein when L is halogen the reaction is conducted in the presence of a suitable amine (such as triethylamine), and when L is OH the reaction is conducted in the presence of a suitable coupling agent (such as PYBROP™). A compound of formula (II) can be prepared by methodology analogous to that described in the Examples below. It will be appreciated that in the process described above other functional groups (such as amine or hydroxy groups) of intermediate compounds may need to be protected by protecting groups. The use of protecting groups is described in 'Protective Groups in Organic Synthesis', 2nd edition, T. W. Greene & P. G. M. Wutz, Wiley-Interscience (1991).

Further compounds of formula (1) can be prepared by adaptation of: the routes described above, methods described in the art or the Examples recited below. The necessary intermediates are either commercially available or can be prepared by using or adapting methods described in the art.

In another aspect the present invention provides processes for the preparation of compounds of formula (I).

The compounds of the invention have activity as pharmaceuticals, in particular as modulators of chemokine receptor (especially CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

In one aspect examples of these conditions are:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behçet's disease, Sjogren's syndrome or systemic sclerosis;
(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitideserythemas, cutaneous eosinophilias, uveitis, Alopecia greata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Imunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

The compounds of the invention are also H1 antagonists and may be used in the treatment of allergic disorders.

The compounds of the invention may also be used to control a sign and/or symptom of what is commonly referred to as a cold (for example a sign and/or symptom of a common cold or influenza or other associated respiratory virus infection).

According to a further feature of the invention there is provided a compound of formula (I), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR3 receptor activity), or antagonising H1, in a warm blooded animal, such as man, in need of such treatment, which comprises administering to said animal an effective amount of a compound of the formula (I), or a pharmaceutically acceptable salt thereof or a solvate thereof.

The invention also provides a compound of the formula (I), or a pharmaceutically acceptable salt thereof or a solvate thereof, for use as a medicament.

In another aspect the invention provides the use of a compound of formula (I), or a pharmaceutically acceptable salt thereof or a solvate thereof, in the manufacture of a medicament for use in therapy (for example modulating chemokine receptor activity (especially CCR3 receptor activity), or antagonising H1, in a warm blooded animal, such as man).

The invention further provides the use of a compound of formula (I), or a pharmaceutically acceptable salt thereof, in the manufacture of a medicament for use in the treatment of:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia greata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a warm blooded animal, such as man.

In a further aspect a compound of formula (I), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicaientosa; membranous rhinitis including croupous, fibrinous or pseudomembranous rhinitis or scrofoulous rhinitis; seasonal rhinitis including rhinitis nervosa (hay fever) or vasomotor rhinitis}.

In a still further aspect a compound of formula (I), or a pharmaceutically acceptable salt thereof, is useful in the treatment of asthma.

The present invention also provides the use of a compound of formula (I), or a pharmaceutically acceptable salt thereof, in the manufacture of a medicament for use in the treatment of asthma or rhinitis.

The present invention further provides a method of treating a chemokine mediated disease state (especially a CCR3 mediated disease state, especially asthma) in a warm blooded animal, such as man, which comprises administering to a mammal in need of such treatment an effective amount of a compound of formula (I), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

Therefore in another aspect the present invention provides a pharmaceutical composition that comprises a compound of the formula (I), or a pharmaceutically acceptable salt thereof or a solvate thereof (active ingredient), and a pharmaceutically acceptable adjuvant, diluent or carrier. In a further aspect the present invention provides a process for the preparation of said composition that comprises mixing active ingredient with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between. 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (D), or a pharmaceutically-acceptable salt thereof (hereafter Compound X), for therapeutic or prophylactic use in humans:

(a)

| Tablet I | mg/tablet |
|---|---|
| Compound X | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1.0 |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)-(c) may be enteric coated by conventional means, for example to provide a coating of cellulose acetate phthalate.

The invention will now be illustrated by the following non-limiting Examples (but not Examples 1 and 2) in which, unless stated otherwise:
(i) when given, $^1$H NMR data is quoted in the form of delta values for major diagnostic protons, given in parts per million (ppm) relative to tetramethylsilane (TMS) as an internal standard;
(ii) mass spectra (MS): generally only ions which indicate the parent mass are reported, and unless otherwise stated the mass ion quoted is the positive mass ion—$(M+H)^+$;
(iii) the title and sub-title compounds of the examples and methods were named using the ACD/name program (version 4.53) from Advanced Chemical Development Inc, Canada;
(iv) unless stated otherwise, reverse phase HPLC was conducted using a Symmetry, NovaPak™ or XTerra™ reverse phase silica column;
(v) solvents were dried with $MgSO_4$ or $Na_2SO_4$; and,
(vi) the following abbreviations are used:

| THF | tetrahydrofuran; |
|---|---|
| Boc | tert-butoxycarbonyl; |
| HPLC | high pressure liquid chromatography; |
| DEAD | diethyl-azodicarboxylate; and, |
| TFA | trifluoroacetic acid. |

EXAMPLE 1

This Example illustrates the preparation of 4-(3,4-dichlorophenoxy)piperidine.

Step a: tert-Butyl 4-(3,4-dichlorophenoxy)-1-piperidinecarboxylate.

Diethyl azodicarboxylate (41 ml) was added to a solution of triphenylphosphine (62.9 g) in tetrahydrofuran (800 ml) at 0° C. After 15 minutes 3,4-dichlorophenol (39.1 g) was added, after a further 15 minutes tert-butyl 4-hydroxy-1-piperidinecarboxylate (48.3 g) in tetrahydrofuran (400 ml) was added dropwise over 30 minutes. The solution was stirred at room temperature for 16 hours and concentrated to a small volume. Purification by flash chromatography (silica) eluting with ethyl acetate: iso-hexane (95:5) gave the sub-title compound as an oil (61.3 g).
MS: APCI (+ve): 246 (M-BOC+2H)

Step b: 4-(3,4-Dichlorophenoxy)piperidine

The product from Step (a) was dissolved in dichloromethane (600 ml) and trifluoroacetic acid (300 ml) was added. After 24 hours at room temperature the solution was evaporated and the resultant gum triturated under ether to give the sub-titled product as a solid (36.6 g). The free base was liberated by addition of aqueous NaOH (2M) and extraction with ethyl acetate followed by evaporation of solvent to give the title compound as a gum (25 g).
$^1$H NMR (CDCl$_3$) δ 1.77 (1H, br s), 2.05-2.26 (4H, m), 3.20-3.49 (4H, m), 4.61 (1H, s), 6.69-7.52 (3H, m).

Other substituted phenoxypiperidines are known in the literature. See, for example, WO 01/77101

EXAMPLE 2

This Example illustrates the preparation of 2-{[4-(3,4-dichlorophenoxy)piperidin-1-yl]methyl}morpholine.

Step a: tert-Butyl 2-{[(methylsulfonyl)oxy]methyl}morpholine-4-carboxylate

To a solution of tert-butyl 2-(hydroxymethyl)morpholinecarboxylate (0.5 g) and N-ethyl-N,N-diisopropylamine (0.2 ml) in dichloromethane (20 ml) at room temperature was added methanesulfonic anhydride (0.48 g). The reaction was stirred for 5 days. The reaction mixture was poured onto saturated aqueous NaHCO$_3$ solution and the organics were extracted with ethyl acetate. The combined organic extracts were washed with brine, dried with MgSO$_4$ and concentrated to give an oil (0.35 g). This was used without further purification.
$^1$H NMR (CDCl$_3$) 1.47 (9H, s), 2.72-3.01 (4H, m), 3.07 (3H, s), 3.55 (1H, t), 3.66-3.74 (1H, m), 3.84-3.98 (3H, m).

Step b: tert-Butyl 2-{[4-(3,4-dichlorophenoxy)piperidin-1-yl]methyl]morpholine-4-carboxylate To a solution of the product from Example 1, Step (b) dissolved in acetonitrile (12 ml) was added the product of Example 2, Step (a). The mixture was refluxed for 12 hrs and the solvents were evaporated. Purification by flash chromatography (silica) eluting with dichloromethane: methanol: NH$_3$ (aq) (2:98:0.1) gave the sub-title compound as an oil (1.9 g).
MS: ES(+ve): 445 (M+H)

Step c: 2-{[4-(3,4-dichlorophenoxy)piperidin-1-yl]methyl}morpholine

The product from Step (b) was dissolved in dichloromethane (30 ml) and trifluoroacetic acid (10 ml) was added. After 4 hours at room temperature the solution was evaporated. The free base was liberated by addition of aqueous NaOH (2M) and extraction with dichloromethane. The combined organic extracts were dried with MgSO$_4$ and concentrated to give an oil (1.47 g).
MS: APCI (+ve): 345 (M+H)

EXAMPLE 3

This Example illustrates the preparation of 2-[(2-{[4-(3,4-dichlorophenoxy)piperidin-1-yl]methyl}morpholin-4-yl)carbonyl]-6-fluoroimidazo[1,2-a]pyridine.

Step a: 6-Fluoro-imidazo[1,2-a]pyridine-2-carboxylic Acid Ethyl Ester

To a solution of 2-amino-5-fluoropyridine (1.12 g) in diethyl ether (25 ml) was added ethyl bromopyruvate (1.25 ml). The mixture was stirred for 1 hour. The resultant solid was filtered off, suspended in ethanol and heated at reflux for 4 hrs. The solvent was removed by evaporation and the residue partitioned between ethyl acetate (100 ml) and aqueous sodium bicarbonate solution (100 ml). The organic layer was separated, dried with MgSO$_4$, and the solvent removed by evaporation. The residue was purified by flash chromatography (silica) eluting with ethyl acetate:hexane (3:1) to give the sub-title compound as a colourless solid (1.12 g).

MS: ES(+ve): 209 (M+H) $^1$H NMR (CDCl$_3$) δ 1.44 (3H, t), 4.46 (2H, q), 7.19 (1H, ddd), 7.68 (1H, dd), 8.07-8.09 (1H, m), 8.19 (1H, s).

Step b: 6-Fluoro-imidazo[1,2-a]pyridine-2-carboxylic Acid

A solution of the product of step (a) (1 g) in 4N HCl was refluxed for 4 hours. The solvent was evaporated to give the sub-title compound as a white solid (0.86 g).

MS: ES(+ve): 181 (M+H) $^1$H NMR (DMSO-D6) δ 7.81-7.89 (2H, m), 8.71 (1H, s), 9.03 (1H, s).

Step c: 6-Fluoroimidazo[1,2-a]pyridine-2-carbonyl Chloride

To a suspension of the product of step (b) (20 g) in toluene (250 ml) and tetrabutylammonium chloride (0.3 g) was added thionyl chloride (40 ml) and the mixture refluxed for 4 hrs. A further aliquot of thionyl chloride-(40 ml) was added and the mixture was refluxed for a further 4 hrs. Solvents were evaporated and the residue was azeotroped with toluene to give the sub-title compound as a solid (20 g). This was used without further purification.

Step d: 2-[(2-{[4-(3,4-dichlorophenoxy)piperidin-1-yl]methyl}morpholin-4-yl)carbonyl]6-fluoroimidazo[1,2-a]pyridine.

The product of Example 2, Step (c) (0.2 g) was dissolved in dichloromethane (4 ml) and triethylamine (0.16 ml) added. The product of Step (c) (0.12 g) was then added and the reaction stirred for 2 hrs. Saturated aqueous NaHCO$_3$ solution was added and the product was extracted with dichloromethane. The combined organic extracts were dried with MgSO$_4$ and concentrated. Purification by reverse phase HPLC (with a gradient eluent system (25% MeCN/NH$_{3(aq)}$ (0.1%) to 95% MeCN/NH$_{3(aq)}$ (0.1%)) gave the title compound (0.024 g).

MS: APCI (+ve): 507 (M+H) $^1$H NMR (CDCl$_3$) δ 1.83 (2H, brs), 1.97 (2H, brs), 2.39-2.42 (3H, m), 2.60-2.76 (3H, m), 2.98-3.12 (1H, m), 3.35-3.44 (1H, m), 3.63-3.75 (2H, m), 3.97-4.05 (1H, m), 4.23-4.30 (1H, m), 4.52-4.65 (1H, m), 5.28-5.37 (1H, m), 6.75 (1H, dd), 7.00 (1H, d), 7.14-7.21 (1H, m), 7.29-7.32 (1H, m), 7.53-7.58 (1H, m), 8.07-8.09 (1H, m), 8.12 (1H, s)

EXAMPLE 4

This Example illustrates the preparation of 2-{[4-(3,4-dichlorophenoxy)piperidin-1-yl]methyl}-4-[3-(methylsulfonyl)benzoyl]morpholine and separation of their enantiomers.

The product of Example 2 Step (c) was coupled with 3-(methylsulfonyl)benzoyl chloride following the procedure of Example 3 step (d) to give the title compound.

MS: APCI (+ve): 527 (M+H)

This mixture of racemates was then purified using a chirapak AD column with hexane: isopropanol (6:4) as eluent to give two enantiomerically pure compounds with unknown absolute configuration. The absolute configuration was established by preparation of one of the enantiomers by the method of Example 5.

EXAMPLE 5

This Example illustrates the preparation of (2S)-2-{[4-(3,4-dichlorophenoxy)piperidin-1-yl]methyl}-4[3-(methylsulfonyl)benzoyl]morpholine Step a: tert-Butyl (2R)-2-{[(methylsulfonyl)oxy]methyl}morpholine-4-carboxylate Prepared in a similar manner to Example 2 Step (a) using tert-butyl (2R)-2-(hydroxymethyl)morpholine-4-carboxylate.

$^1$H NMR (CDCl$_3$) δ 1.47 (9H, s), 2.78 (1H, br s), 2.95 (1H, br s), 3.07 (3H, s), 3.55 (1H, td), 3.67-3.72 (1H, m), 3.90-3.93 (3H, m), 4.24 (2H, d).

Step b: tert-Butyl (2S)-2-{[4-(3,4-dichlorophenoxy)piperidin-1-yl]methyl}morpholine-4-carboxylate Prepared in a similar manner to Example 2 Step (b) using the product of Step (a).

MS: ES (+ve): 389 (M-tert-butyl).

Step c: (2R)-2-{[4-(3,4-Dichlorophenoxy)piperidin-1-yl]methyl}morpholine

Prepared in a similar manner to Example 2 Step (c) using the product of Step (b).

$^1$H NMR (CDCl$_3$) δ 1.77-1.86 (4H, m), 1.95-2.01 (2H, m), 2.26 (1H, dd), 2.35 (2H, t), 2.48-2.57 (2H, m), 2.73 (2H, s), 2.82-2.93 (2H, m), 3.56-3.66 (2H, m), 3.87-3.90 (1H, m), 4.26 (1H, in), 6.75 (1H, dd), 6.99 (1H, d), 7.30 (1H, d).

Step d: (2S)-2-{[4-(3,4-Dichlorophenoxy)piperidin-1-yl]methyl}-4-[3-(methylsulfonyl)benzoyl]morpholine The product of Example 5 Step (c) was coupled with 3-(methylsulfonyl)benzoyl chloride following the procedure of Example 3 Step (d) to give the title compound.

MS: APCI (+ve): 527 (M+H) $^1$H NMR (CDCl$_3$) δ 1.59°-1.86 (7H, m), 2.37-2.73 (7H, m), 3.08 (3H, s), 3.59 (3H, s), 4.25 (1H, s), 6.75 (1H, d), 6.99 (1H, s), 7.30 (1H, d), 7.64-7.72 (2H, m), 8.00-8.04 (2H, m)

$[α]_D^{25}$=+15.70 (c 0 .16, CHCl$_3$).

The Examples 6-72 are examples of compounds of formula (I) and were prepared by the following general method:

The product of Example 2 Step (c) was dissolved in 1-methylpyrrolidin-2-one. (as solvent) with triethylamine (3 molar equivalents) and the appropriate acid of formula HO-T-(W)$^n$—R$^2$ (1 molar equivalents). Bromo-tris-pyrrolidino-phosphonium hexafluorophosphate (PYBROP™, 1.5 molar equivalents) was then added and the reaction left for 24 hrs. Evaporation of solvent and purification by reverse phase HPLC (with a gradient eluent system (25% MeCN/NH$_{3(aq)}$ (0.1%) to 95% MeCN/NH$_{3(aq)}$ (0.1%)) gave the Examples 6-72.

All of Examples 6-72 are compounds wherein X is O and T is C(O); and for:

Example 13 m is 1 and W is CH(CH$_3$);

Example 22 m is 1 and W is cyclopropyl;

Examples 29, 35, 39, 40, 44, 45, 47, 50, 51, 60, 62, 63, 64, 67 and 72 W is CH$_2$;

Examples 23 and 31 m is 1 and W is (CH$_2$)$_2$;

Example 42 m is 1 and W is CH(CH$_3$)O; and,

For the remaining Examples m is 0.

| Example | Name | (M + H) |
|---|---|---|
| 6 | N-{4-[(2-{[4-(3,4-dichlorophenoxy)piperidin-1-yl]methyl}morpholin-4-yl)carbonyl]phenyl}acetamide | 506 |
| 7 | 2-{[4-(3,4-dichlorophenoxy)piperidin-1-yl]methyl}-4-(1,2,3,4-tetrahydronaphthalen-2-ylcarbonyl)morpholine | 503 |
| 8 | methyl 4-[(2-{[4-(3,4-dichlorophenoxy)piperidin-1-yl]methyl}morpholin-4-yl)carbonyl]benzoate | 507 |
| 9 | 3-[(2-{[4-(3,4-dichlorophenoxy)piperidin-1-yl]methyl}morpholin-4-yl)carbonyl]-1-ethyl-7-methyl-1,8-naphthyridin-4(1H)-one | 559 |
| 10 | 4-[(2-{[4-(3,4-dichlorophenoxy)piperidin-1-yl]methyl}morpholin-4-yl)carbonyl]benzonitrile | 474 |
| 11 | 2-{[4-(3,4-dichlorophenoxy)piperidin-1-yl]methyl}-4-(1H-pyrazol-4-ylcarbonyl)morpholine | 439 |
| 12 | 2-{[4-(3,4-dichlorophenoxy)piperidin-1-yl]methyl}-4-[(5-pyridin-2-ylthien-2-yl)carbonyl]morpholine | 532 |
| 13 | 2-{[4-(3,4-dichlorophenoxy)piperidin-1-yl]methyl}-4-[2-(2-fluoro-1,1'-biphenyl-4-yl)propanoyl]morpholine | 571 |
| 14 | 2-[(2-{[4-(3,4-dichlorophenoxy)piperidin-1-yl]methyl}morpholin-4-yl)carbonyl]-3-fluoroaniline | 482 |
| 15 | 5-[(2-{[4-(3,4-dichlorophenoxy)piperidin-1-yl]methyl}-morpholin-4-yl)carbonyl]-2-(ethylthio)pyrimidin-4-amine | 526 |
| 16 | 3-[(2-{[4-(3,4-dichlorophenoxy)piperidin-1-yl]methyl}-morpholin-4-yl)carbonyl]-4,7-dimethylpyrazolo[5,1-c][1,2,4]triazine | 519 519 |
| 17 | 2-{[4-(3,4-dichlorophenoxy)piperidin-1-yl]methyl}-4-[(5-methyl-3-phenylisoxazol-4-yl)carbonyl]morpholine | 530 |
| 18 | 2-{[4-(3,4-dichlorophenoxy)piperidin-1-yl]methyl}-4-[(1-oxidopyridin-3-yl)carbonyl]morpholine | 466 |
| 19 | 2-{[4-(3,4-dichlorophenoxy)piperidin-1-yl]methyl}-4-[(3,5-dimethylisoxazol-4-yl)carbonyl]morpholine | 468 |
| 20 | 6-[(2-{[4-(3,4-dichlorophenoxy)piperidin-1-yl]methyl}morpholin-4-yl)carbonyl]-9H-purine | 491 |
| 21 | 2-{[4-(3,4-dichlorophenoxy)piperidin-1-yl]methyl}-4-[(5-methyl-1-phenyl-1H-pyrazol-4-yl)carbonyl]morpholine | 529 |
| 22 | 2-{[4-(3,4-dichlorophenoxy)piperidin-1-yl]methyl}-4-{[(2R)-2-phenylcyclopropyl]carbonyl}morpholine | 489 |
| 23 | 2-{[4-(3,4-dichlorophenoxy)piperidin-1-yl]methyl}-4-(3-piperidin-1-ylpropanoyl)morpholine | 484 |
| 24 | 6-[(2-{[4-(3,4-dichlorophenoxy)piperidin-1-yl]methyl}-morpholin-4-yl)carbonyl]-2,7-dimethylpyrazolo[1,5-a]pyrimidine | 518 |
| 25 | 4-(1-benzothien-2-ylcarbonyl)-2-{[4-(3,4-dichlorophenoxy)piperidin-1-yl]methyl}morpholine | 505 |
| 26 | 2-{[4-(3,4-dichlorophenoxy)piperidin-1-yl]methyl}-4-[(2,4-dimethyl-1,3-thiazol-5-yl)carbonyl]morpholine | 484 |
| 27 | 2-{[4-(3,4-dichlorophenoxy)piperidin-1-yl]methyl}-4-(3-fluoro-2-methylbenzoyl)morpholine | 481 |
| 28 | 1-benzyl-3-[(2-{[4-(3,4-dichlorophenoxy)piperidin-1-yl]methyl}morpholin-4-yl)carbonyl]pyridin-2(1H)-one | 556 |
| 29 | 2-{[4-(3,4-dichlorophenoxy)piperidin-1-yl]methyl}-4-(1H-imidazol-4-ylacetyl)morpholine | 453 |
| 30 | 5-[(2-{[4-(3,4-dichlorophenoxy)piperidin-1-yl]methyl}-morpholin-4-yl)carbonyl]-1-methylpyridin-2(1H)-one | 480 |
| 31 | 2-{[4-(3,4-dichlorophenoxy)piperidin-1-yl]methyl}-4-[3-(3-pyridin-2-yl-1,2,4-oxadiazol-5-yl)propanoyl]morpholine | 546 |
| 32 | methyl 3-[(2-{[4-(3,4-dichlorophenoxy)piperidin-1-yl]methyl}morpholin-4-yl)carbonyl]pyridine-2-carboxylate | 508 |
| 33 | 2-{[4-(3,4-dichlorophenoxy)piperidin-1-yl]methyl}-4-[(4-methyl-2-pyrazin-2-yl-1,3-thiazol-5-yl)carbonyl]morpholine | 548 |
| 34 | 4-[(2-{[4-(3,4-dichlorophenoxy)piperidin-1-yl]methyl}-morpholin-4-yl)carbonyl]-1,2-dihydro-3H-indazol-3-one | 505 |
| 35 | 2-{[4-(3,4-dichlorophenoxy)piperidin-1-yl]methyl}-4-[(4-methylphenyl)acetyl]morpholine | 477 |
| 36 | 2-{[4-(3,4-dichlorophenoxy)piperidin-1-yl]methyl}-4-(isoxazol-5-ylcarbonyl)morpholine | 440 |
| 37 | N-{4-[(2-{[4-(3,4-dichlorophenoxy)piperidin-1-yl]methyl}-morpholin-4-yl)carbonyl]-1,3-thiazol-2-yl}acetamide | 513 |
| 38 | 2-{[4-(3,4-dichlorophenoxy)piperidin-1-yl]methyl}-4-(1-oxidoisonicotinoyl)morpholine | 466 |
| 39 | 2-{[4-(3,4-dichlorophenoxy)piperidin-1-yl]methyl}-4-[(3,4-difluorophenyl)acetyl]morpholine | 499 |
| 40 | 4-[2-(2-{[4-(3,4-dichlorophenoxy)piperidin-1-yl]methyl}morpholin-4-yl)-2-oxoethyl]phthalazin-1(2H)-one | 531 |
| 41 | N-{4-[(2-{[4-(3,4-dichlorophenoxy)piperidin-1-yl]methyl}-morpholin-4-yl)carbonyl]phenyl}methanesulfonamide | 542 |
| 42 | 2-{[4-(3,4-dichlorophenoxy)piperidin-1-yl]methyl}-4-(2-phenoxypropanoyl)morpholine | 493 |

-continued

| Example | Name | (M + H) |
|---|---|---|
| 43 | 6-[(2-{[4-(3,4-dichlorophenoxy)piperidin-1-yl]methyl}-morpholin-4-yl)carbonyl]-4,5-dihydropyridazin-3(2H)-one | 469 |
| 44 | 1-[2-(2-{[4-(3,4-dichlorophenoxy)piperidin-1-yl]methyl}-morpholin-4-yl)-2-oxoethyl]-5-methylpyrimidine-2,4(1H,3H)-dione | 511 |
| 45 | 4-(2-{[4-(3,4-dichlorophenoxy)piperidin-1-yl]methyl}-morpholin-4-yl)-4-oxobutan-2-ol | 431 |
| 46 | 4-[(2-{[4-(3,4-dichlorophenoxy)piperidin-1-yl]methyl}morpholin-4-yl)carbonyl]isoquinolin-1(2H)-one | 516 |
| 47 | 2-{[4-(3,4-dichlorophenoxy)piperidin-1-yl]methyl}-4-[(3-methyl-1H-1,2,4-triazol-5-yl)acetyl]morpholine | 468 |
| 48 | 7-[(2-{[4-(3,4-dichlorophenoxy)piperidin-1-yl]methyl}-morpholin-4-yl)carbonyl]-2H-1,4-benzoxazin-3(4H)-one | 520 |
| 49 | (1S)-2-[(2-{[4-(3,4-dichlorophenoxy)piperidin-1-yl]methyl}morpholin-4-yl)carbonyl]cyclopentanol | 457 |
| 50 | 2-{[4-(3,4-dichlorophenoxy)piperidin-1-yl]methyl}-4-[(3,5-difluorophenyl)acetyl]morpholine | 499 |
| 51 | 1-[2-(2-{[4-(3,4-dichlorophenoxy)piperidin-1-yl]methyl}morpholin-4-yl)-2-oxoethyl]-3-ethyl-1,3-dihydro-2H-benzimidazol-2-one | 547 |
| 52 | {3-[(2-{[4-(3,4-dichlorophenoxy)piperidin-1-yl]methyl}-morpholin-4-yl)carbonyl]-1H-pyrazol-4-yl}methanol | 469 |
| 53 | N-{2-[(2-{[4-(3,4-dichlorophenoxy)piperidin-1-yl]methyl}-morpholin-4-yl)carbonyl]phenyl}-1,3-dimethyl-1H-pyrazol-5-amine | 558 |
| 54 | 4-[(2-{[4-(3,4-dichlorophenoxy)piperidin-1-yl]methyl}-morpholin-4-yl)carbonyl]-1-methyl-1H-pyrazol-5-amine | 468 |
| 55 | 5-[(2-{[4-(3,4-dichlorophenoxy)piperidin-1-yl]methyl}morpholin-4-yl)carbonyl]-1,3-dimethyl-1H-thieno[2,3-c]pyrazole | 523 |
| 56 | 2-{[4-(3,4-dichlorophenoxy)piperidin-1-yl]methyl}-4-{[3-(trifluoromethyl)-1H-pyrazol-4-yl]carbonyl}morpholine | 507 |
| 57 | 2-{[4-(3,4-dichlorophenoxy)piperidin-1-yl]methyl}-4-[4-(2H-tetraazol-5-yl)benzoyl]morpholine | 517 |
| 58 | 1-{4-[(2-{[4-(3,4-dichlorophenoxy)piperidin-1-yl]methyl}morpholin-4-yl)carbonyl]phenyl}pyrrolidin-2-one | 532 |
| 59 | 2-{[4-(3,4-dichlorophenoxy)piperidin-1-yl]methyl}-4-[(3-phenylisoxazol-5-yl)carbonyl]morpholine | 516 |
| 60 | 2-{[4-(3,4-dichlorophenoxy)piperidin-1-yl]methyl}-4-{[4-(methylsulfonyl)phenyl]acetyl}morpholine | 541 |
| 61 | 2-{[4-(3,4-dichlorophenoxy)piperidin-1-yl]methyl}-4-{[5-(methylsulfonyl)thien-2-yl]carbonyl}morpholine | 533 |
| 62 | 8-[2-(2-{[4-(3,4-dichlorophenoxy)piperidin-1-yl]methyl}-morpholin-4-yl)-2-oxoethyl]-1,3-dimethyl-3,7-dihydro-1H-purine-2,6-dione | 565 |
| 63 | 2-{[4-(3,4-dichlorophenoxy)piperidin-1-yl]methyl}-4-[(2-methyl-4-thien-2-yl-1,3-thiazol-5-yl)acetyl]morpholine | 566 |
| 64 | 2-[2-(2-{[4-(3,4-dichlorophenoxy)piperidin-1-yl]methyl}morpholin-4-yl)-2-oxoethyl]benzonitrile | 488 |
| 65 | 4-[(2-{[4-(3,4-dichlorophenoxy)piperidin-1-yl]methyl}morpholin-4-yl)carbonyl]-1,5-dimethyl-2-phenyl-1,2-dihydro-3H-pyrazol-3-one | 559 |
| 66 | 2-{[4-(3,4-dichlorophenoxy)piperidin-1-yl]methyl}-4-{[3-methyl-5-(trifluoromethyl)isoxazol-4-yl]carbonyl}morpholine | 522 |
| 67 | 1-[2-(2-{[4-(3,4-dichlorophenoxy)piperidin-1-yl]methyl}-morpholin-4-yl)-2-oxoethyl]-1H-1,2,3-benzotriazole | 504 |
| 68 | 2-{[4-(3,4-dichlorophenoxy)piperidin-1-yl]methyl}-4-{[2-(methylsulfinyl)thien-3-yl]carbonyl}morpholine | 517 |
| 69 | 3-[(2-{[4-(3,4-dichlorophenoxy)piperidin-1-yl]methyl}-morpholin-4-yl)carbonyl]-1-methylpyridin-2(1H)-one | 480 |
| 70 | 3-{4-[(2-{[4-(3,4-dichlorophenoxy)piperidin-1-yl]methyl}morpholin-4-yl)carbonyl]phenyl}-1H-indazole | 565 |
| 71 | 2-[(2-{[4-(3,4-dichlorophenoxy)piperidin-1-yl]methyl}-morpholin-4-yl)carbonyl]-4,6-dimethylthieno[2,3-b]pyridin-3-amine | 549 |
| 72 | 4-[2-(2-{[4-(3,4-dichlorophenoxy)piperidin-1-yl]methyl}morpholin-4-yl)-2-oxoethyl]benzenesulfonamide | 542 |

EXAMPLE 73

This Example illustrates the preparation of 4-[((2R)-2-{([4-(3,4-dichlorophenoxy)piperidin-1-yl]methyl}morpholin-4-yl)carbonyl]isoquinolin-1 (2H)-one.

To a stirred solution of (2S)-2-{[4-(3,4-dichlorophenoxy)piperidin-1-yl]methyl}morpholine (0.170 g; prepared analogously to the enantiomer, Example 5 Steps a-c) and diisopropylethylamine (0.103 mL) in dichloromethane (0.3 mL) was added 1-oxo-1,2-dihydroisoquinoline-4-carbonyl chloride (0.107 g) at RT and the solution was stirred for 17 h. Saturated sodium bicarbonate solution (25 mL) was added and the product was extracted into ethyl acetate (20 mL×3). Silica gel was added and the solvent was evaporated. The resultant powder was loaded onto a 3 cm plug of silica gel and product was eluted (eluent 97:3 dichloromethane/7N $NH_3$ in MeOH). Further purification using RPHPLC (10% MeCN/90% $NH_4OAc$ aq (0.1%) gradient to 70% MeCN/30% $NH_4OAc$) provided the title compound as a white solid (0.100 g).

MS: APCI(+ve): 516 (M+H) $^1H$ NMR δ (DMSO at 90° C.) 1.41-1.59 (2H, m), 1.72-1.83 (2H, m), 1.87-1.91 (3H, m), 2.16-2.31 (2H, m), 2.37 (1H, t), 2.54-2.67 (2H, m), 2.82 (1H, dd), 3.01-3.13 (1H, m), 3.43-3.61 (2H, m), 3.77-4.03 (2H, m), 4.26-4.38 (1H, m), 6.92 (1H, dd), 7.16 (1H, d), 7.21 (1H, s), 7.44 (1H, d), 7.50-7.60 (2H, m), 7.73 (1H, td), 8.25 (1H, ddd).

EXAMPLE 74

Pharmacological Analysis: Calcium Flux $[Ca^{2+}]_i$ Assay

Human Eosinophils

Human eosinophils were isolated from EDTA anticoagulated peripheral blood as previously described (Hansel et al., *J. Immunol. Methods*, 1991, 145, 105-110). The cells were resuspended ($5\times10^6$ $ml^{-1}$) and loaded with 5 μM FLUO-3/AM+Pluronic F127 2.2 μl/ml (Molecular Probes) in low potassium solution (LKS; NaCl 118 mM, $MgSO_4$ 0.8 mM, glucose 5.5 mM, $Na_2CO_3$ 8.5 mM, KCl 5 mM, HEPES 20 mM, $CaCl_2$ 1.8 mM, BSA 0.1%, pH 7.4) for one hour at room temperature. After loading, cells were centrifuged at 200 g for 5 min and resuspended in LKS at $2.5\times10^6$ $ml^{-1}$. The cells were then transferred to 96 well FLIPr plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1%(v/v) DMSO. Assays were initiated by the addition of an $A_{50}$ concentration of eotaxin and the transient increase in fluo-3 fluorescence ($1_{Ex}$=490 nm and $1_{Em}$=520 nm) monitored using a FLIPR (Fluorometric Imaging Plate Reader, Molecular Devices, Sunnyvale, U.S.A.).

Compounds of the Examples were found to be antagonists if the increase in fluorescence induced by eotaxin (a selective CCR3 agonist) was inhibited in a concentration dependent manner. The concentration of antagonist required to inhibit the fluorescence by 50% can be used to determine the $IC_{50}$ for the antagonist at the CCR3 receptor.

EXAMPLE 75

Human Eosinophil Chemotaxis

Human eosinophils were isolated from EDTA anticoagulated peripheral blood as previously described (Hansel et al., *J. Immunol. Methods*, 1991, 145, 105-110). The cells were resuspended at $10\times10^6$ $ml^{-1}$ in RPMI containing 200 μg/ml penicillin, 200 μg/ml streptomycin sulfate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3 μm pore, Neuroprobe) was loaded by adding 28 μl of a concentration of eotaxin 0.1 to 100 nM (a selective CCR3 agonist over this concentration range) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton×100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

Compounds of the Examples were found to be antagonists of eotaxin mediated human eosinophil chemotaxis if the concentration response to eotaxin was shifted to the right of the control curve. Measuring the concentration of eotaxin required to give 50% chemotaxis in the presence or absence of compounds enables the apparent affinity of the compounds at CCR3 to be calculated.

| Example | % inhibition at 1 μM |
|---------|----------------------|
| 5       | >75                  |
| 73      | >75                  |

EXAMPLE 76

Guinea-Pig Isolated Trachea (See for example, Harrison, R. W. S., Carswell, H. & Young, J. M. (1984) European J. Pharmacol., 106, 405-409.)

Male albino Dunkin-Hartley guinea-pigs (250 g) were killed by cervical dislocation and the whole trachea removed. After clearing the adherent connective tissue, the trachea was, cut into six ring segments each three cartilage bands wide and then suspended in 20 ml organ baths containing Krebs-Henseleit solution of the following composition (mM): NaCl 117.6, $NaH_2PO_4$ 0.9, $NaHCO_3$ 25.0, $MgSO_4$ 1.2, KCl 5.4, $CaCl_2$ 2.6 and glucose 11.1. The buffer was maintained at 37° C. and gassed with 5% $CO_2$ in oxygen. Indomethacin (2.8 μM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 $log_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies (p[A$_{50}$] values) of histamine in the absence and presence of the test compound. Affinity (pA$_2$) values of test compounds were subsequently calculated using the following equation:

$$\log(r-1)=\log[B]+pA_2$$

where r=[A]$_{50}$ in presence of test compound/[A]$_{50}$ in absence of antagonist and [B] is the concentration of test compound. Compounds of the Examples were found to be H1 antagonists.

EXAMPLE 77

Histamine H1 receptor binding activity of compounds of the invention was assessed by competition displacement of 1 nM [3H]-pyrilamine (Amersham, Bucks, Product code TRK 608, specific activity 30Ci/mmol) to 2 µg membranes prepared from recombinant CHO-K1 cells expressing the human H1 receptor (Furoscreen S A, Brussels, Belgium, product code ES-390-M) in assay buffer (50 mM Tris pH 7.4 containing 2 mM MgCl$_2$, 250 mM sucrose and 100 mM NaCl) for 1 hour at room temperature.

| Example | H1 pKi/ [1328_S] |
|---------|------------------|
| 3       | 7.9              |
| 4       | 7.0              |
| 5       | 7.7              |
| 73      | 8.1              |

The invention claimed is:
1. A compound of formula (I):

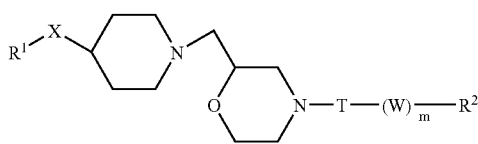

T is C(O) or S(O)$_2$;
W is CH$_2$, (CH$_2$)$_2$, CH(CH$_3$), CH(CH$_3$)O or cyclopropyl;
X is O, CH$_2$, C(O), S, S(O), S(O)$_2$ or NR$^3$;
m is 0 or 1;
R$^1$ is optionally substituted aryl or optionally substituted heterocyclyl;
R$^2$ is alkyl (optionally substituted by OH), cycloalkyl, optionally substituted aryl or optionally substituted heterocyclyl;
wherein the foregoing aryl and heterocyclyl moieties are optionally substituted by:
halogen, cyano, nitro, hydroxy, oxo, S(O)$_p$R$^4$, OC(O)NR$^5$R$^6$, NR$^7$R$^8$, NR$^9$C(O)R$^{10}$, NR$^{11}$C(O)NR$^{12}$R$^{13}$, S(O)$_2$NR$^{14}$R$^{15}$, NR$^{16}$S(O)$_2$R$^{17}$, C(O)NR$^{18}$R$^{19}$, C(O)R$^{20}$, C$^{21}$, NR$^{22}$CO$_2$R$^{23}$, C$_{1-6}$ alkyl, C$_{1-6}$ haloalkyl, C$_{1-6}$ alkoxy(C$_{1-6}$)alkyl, C$_{1-6}$ alkoxy, C$_{1-6}$ haloalkoxy, C$_{1-6}$ alkoxy(C$_{1-6}$)alkoxy, C$_{1-6}$ alkylthio, C$_{2-6}$ alkenyl, C$_{2-6}$ alkynyl, C$_{3-10}$ cycloalkyl (itself optionally substituted by C$_{1-4}$ alkyl or oxo), methylenedioxy, difluoromethylenedioxy, phenyl, phenyl(C$_{1-4}$)alkyl, phenoxy, phenylthio, phenyl(C$_{1-4}$)alkoxy, heteroaryl, heteroaryl(C$_{1-4}$)alkyl, heteroaryloxy or heteroaryl(C$_{1-4}$)alkoxy;
wherein any of the immediately foregoing phenyl and heteroaryl moieties are optionally substituted with halogen, hydroxy, nitro, S(O)$_q$(C$_{1-4}$alkyl), S(O)$_2$NH$_2$, cyano, C$_{1-4}$ alkyl, C$_{1-4}$ alkoxy, C(O)NH$_2$, C(O)NH(C$_{1-4}$alkyl), CO$_2$H, CO$_2$(C$_{1-4}$alkyl), NHC(O)(C$_{1-4}$alkyl), NHS(O)$_2$(C$_{1-4}$alkyl), C(O)(C$_{1-4}$alkyl), CF$_3$ or OCF$_3$;
p and q are, independently, 0, 1 or 2;
R$^3$, R$^5$, R$^6$, R$^7$, R$^8$, R$^9$, R$^{10}$, R$^{11}$, R$^{12}$, R$^{13}$, R$^{14}$, Re$^{15}$, R$^{16}$, R$^{18}$, R$^{19}$ R$^{20}$, R$^{21}$ and R$^{22}$ are, independently, hydrogen, C$_{1-6}$ alkyl (optionally substituted by halogen, hydroxy or C$_{3-10}$ cycloalkyl), CH$_2$(C$_{2-6}$ alkenyl), phenyl (itself optionally substituted by halogen, hydroxy, nitro, NH$_2$, NH(C$_{1-4}$ alkyl), N(C$_{1-4}$alkyl)$_2$, S(O)$_2$(C$_{1-4}$ alkyl), S(O)$_2$NH$_2$, cyano, C$_{1-4}$ alkyl, C$_{1-4}$ alkoxy, C(O)NH$_2$, C(O)NH(C$_{1-4}$ alkyl), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, NH$_2$, NH(C$_{1-4}$ alkyl), N(C$_{1-4}$ alkyl)$_2$, S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$, cyano, C$_{1-4}$ alkyl, C$_{1-4}$ alkoxy, C(O)NH$_2$, C(O)NH(C$_{1-4}$ alkyl), C(O)N (C$_{1-4}$ alkyl)$_2$, CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$);
alternatively NR$^5$R$^6$, NR$^7$R$^8$, NR$^{12}$R$^{13}$, NR$^{14}$R$^{15}$, NR$^{18}$R$^{19}$ or groups N(C$_{1-4}$alkl)$_2$ may, independently, form a 4-7 membered heterocyclic ring, azetidine, pyrrolidine, piperidine, azepine, 1,4-morpholine or 1,4-piperazine, the latter optionally substituted by C$_{1-4}$alkyl on the distal nitrogen;
R$^4$, R$^{17}$ and R$^{23}$ are, independently, C$_{1-6}$ alkyl (optionally substituted by halogen, hydroxy or C$_{3-10}$ cycloalkyl), CH$_2$(C$_{2-6}$ alkenyl), phenyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ above), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ above), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ above), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ above), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ above), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ above), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$);
or an N-oxide thereof; or a pharmaceutically acceptable salt thereof; or a solvate thereof.

2. A compound of formula (I) as claimed in claim 1 wherein X is O.

3. A compound of formula (I) as claimed in claim 1 wherein R$^1$ is phenyl substituted with one or more of fluorine, chlorine, C$_{1-4}$ alkyl or C$_{1-4}$ alkoxy.

4. A compound of formula (I) as claimed in claim 1 wherein T is C(O).

5. A compound of formula (I) as claimed in claim 1 wherein m is 1 and W is $CH_2$.

6. A compound of formula (I) as claimed in claim 1 wherein m is 0.

7. A compound of formula (I) as claimed in claim 1 wherein $R^2$ is phenyl optionally substituted by: halo, hydroxy, nitro, cyano, amino, $C_{1-4}$ alkyl (itself optionally substituted by $S(O)_2$phenyl), $C_{1-4}$ alkoxy, $S(O)_kR^{24}$ (wherein k is 0, 1 or 2; and $R^{24}$ is $C_{1-4}$ alkyl or phenyl) or $C_{1-4}$haloalkylthio.

8. A compound of formula (I) as claimed in claim 1 wherein $R^2$ is optionally substituted heterocyclyl; wherein heterocyclyl is thienyl, thiazolyl, pyrazolyl, isoxazolyl, 1,2,4-oxadiazolyl, 1,2,3-triazolyl, tetrazolyl, imidazolyl, pyridinyl, pyridazinyl, pyrimidinyl, benz[b]thienyl, indazolyl, benzimidazolyl, benztriazolyl, benzoxazolyl, imidazo[1,2a]pyridinyl, [1,8]naphthyridinyl, isoquinolinyl, thieno [2,3-b]pyridinyl, pyrazolo[5,1-c][1,2,4]triazinyl, purinyl, pyrazolo[1,5-a]pyrimidinyl, thieno[2,3-c]pyrazolyl or phthalazinyl; and heterocyclyl is optionally substituted by halogen, $C_{1-4}$ alkyl, $C_{1-4}$ alkylthio, phenyl, thienyl, pyridinyl, $CF_3$, $NH_2$, $CO_2(C_{1-4}$ alkyl) or oxo.

9. A pharmaceutical composition comprising a compound of the formula (I), or a pharmaceutically acceptable salt thereof or a solvate thereof and a pharmaceutically acceptable adjuvant, diluent or carrier.

10. A compound of the formula (I) as claimed in claim 1, or a pharmaceutically acceptable salt thereof or a solvate thereof, for use in therapy.

* * * * *